United States Patent
Dorn (10) Patent No.: US 10,299,754 B2
(45) Date of Patent: May 28, 2019

(54) WED DETERMINATION SPATIALLY-RESOLVED IN THE HEAD-FOOT DIRECTION

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/031,295

(22) Filed: Jul. 10, 2018

(65) Prior Publication Data

US 2019/0015065 A1 Jan. 17, 2019

(30) Foreign Application Priority Data

Jul. 12, 2017 (EP) ..................................... 17180981

(51) Int. Cl.
*A61B 6/00* (2006.01)
*A61B 6/03* (2006.01)
*G06T 7/00* (2017.01)
*G16H 30/20* (2018.01)

(52) U.S. Cl.
CPC .............. *A61B 6/544* (2013.01); *A61B 6/032* (2013.01); *A61B 6/488* (2013.01); *A61B 6/5252* (2013.01); *G06T 7/0014* (2013.01); *G16H 30/20* (2018.01)

(58) Field of Classification Search
CPC .......... A61B 6/544; A61B 6/02; A61B 6/032; A61B 6/488; A61B 6/5252
See application file for complete search history.

(56) References Cited

U.S. PATENT DOCUMENTS

| 2004/0202277 | A1 | 10/2004 | Okumura | |
| 2012/0230576 | A1* | 9/2012 | Rohler | A61B 6/032 382/132 |
| 2014/0270053 | A1* | 9/2014 | Larson | A61B 6/032 378/4 |
| 2017/0143291 | A1 | 5/2017 | Guntzer et al. | |

FOREIGN PATENT DOCUMENTS

WO WO 2017103238 A1 6/2017

OTHER PUBLICATIONS

McCollough, Cynthia et al.: "Use of Water Equivalent Diameter for Calculating Patient Size and Size-Specific Dose Estimates (SSDE) in CT"; in: AAPM Rep.; pp. 6-23; XP055446368; 2014.; 2014.
Extended European search report #17180981.7 dated Feb. 8, 2018.

* cited by examiner

*Primary Examiner* — Chih-Cheng Kao
(74) *Attorney, Agent, or Firm* — Harness, Dickey & Pierce, P.L.C.

(57) ABSTRACT

In at least one embodiment, X-ray images of a human examination object acquired via X-ray equipment are each spatially-resolved in a plurality of dimensions. In each case, one dimension extends in the head-foot direction of the examination object. The respective body region is detected in the X-ray images in steps that are equidistant in the head-foot direction and, based on this, the water-equivalent diameter of the examination object is determined in a plane orthogonal to the head-foot direction. The water equivalent diameters determined for each respective position is stored with allocation to the X-ray images and the respective position in the head-foot direction.

14 Claims, 5 Drawing Sheets

WED DETERMINATION SPATIALLY-RESOLVED IN THE HEAD-FOOT DIRECTION

PRIORITY STATEMENT

The present application hereby claims priority under 35 U.S.C. § 119 to European patent application number EP17180981.7 filed Jul. 12, 2017, the entire contents of which are hereby incorporated herein by reference.

FIELD

At least one embodiment of the present invention generally relates to an evaluation method for a number of X-ray images of a human examination object acquired via X-ray equipment,
wherein the X-ray images are each spatially-resolved in a plurality of dimensions,
wherein in each case one dimension extends in the head-foot direction of the examination object.

At least one embodiment of the present invention generally relates to a computer program for an arithmetic device, wherein the computer program comprises machine code, which can be processed by the arithmetic device, wherein processing of the machine code by the arithmetic device causes the arithmetic device to carry out an evaluation method of this kind.

At least one embodiment of the present invention generally relates to an arithmetic device, which is programmed with a computer program of this kind such that during operation it carries out an evaluation method of this kind.

BACKGROUND

Correct determination of doses applied during the course of X-ray examinations is becoming increasingly more important. In the past, a two-dimensional X-ray image (topogram) is conventionally acquired first and in advance for a three-dimensional scan, with one dimension extending in the head-foot direction of the examination object. In this X-ray image, particular two-dimensional regions are selected—automatically or specified by a user—and a water-equivalent diameter of the examination object is uniformly determined for these regions for the respective region. The X-ray dose is then defined using the two-dimensional X-ray image.

An evaluation method is known for example from the publication by the American Association of Physicists in Medicine (2014): "Use of Water Equivalent Diameter for Calculating Patient Size and Size-Specific Dose Estimates (SSDE) in CT (Task Group 220)".

SUMMARY

The inventor has discoverd that the procedure of the past is disadvantageous from various perspectives. Thus the diameter is firstly determined, which is resolved only very roughly in the head-foot direction. Furthermore, an allocation to particular table positions, at which examinations are to be subsequently performed, is not readily discernible.

The inventor has discoverd that the procedure known from the scientific paper (the publication by the American Association of Physicists in Medicine (2014) described above) already works quite well, but it can still be improved.

At least one embodiment of the present invention resides in creating possibilities by which at least one of these drawbacks can be avoided.

At least one embodiment is achieved by an evaluation method. Advantageous embodiments of the evaluation method are also disclosed.

According to at least one embodiment of the invention, an evaluation method comprises
detecting the respective body region in the X-ray images in steps that are equidistant in the head-foot direction and, based on this,
determining the water-equivalent diameter of the examination object in a plane orthogonal to the head-foot direction, and
storing the water-equivalent diameters determined for the respective position with allocation to the X-ray images and the respective position in the head-foot direction.

At least one embodiment is also directed to a computer program and/or non-transitory computer readable medium. According to at least one embodiment of the invention, processing of the machine code by the arithmetic device, causes the arithmetic device to carry out at least one embodiment of an inventive evaluation method.

At least one embodiment is also directed to an arithmetic device. According to at least one embodiment of the invention, the arithmetic device is programed with an least one embodiment of an inventive computer program, so during operation it carries out at least one embodiment of an inventive evaluation method.

BRIEF DESCRIPTION OF THE DRAWINGS

The above-described properties, features and advantages of this invention and the manner in which they are achieved will become clearer and more comprehensible in conjunction with the following description of the example embodiments, which will be illustrated in more detail in conjunction with the drawings, in which schematically.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention, an evaluation method comprises detecting the respective body region in the X-ray images in steps that are equidistant in the head-foot direction and, based on this, determining the water-equivalent diameter of the examination object in a plane orthogonal to the head-foot direction, and storing the water-equivalent diameters determined for the respective position with allocation to the X-ray images and the respective position in the head-foot direction.

The water-equivalent diameter of the examination object describes the overall attenuation of X-ray radiation by the examination object standardized to the attenuation of water. The water-equivalent diameter of the examination object can be defined in particular as the diameter of a water cylinder, wherein, with computed tomography imaging, the water cylinder causes the same overall attenuation of the X-ray intensity as the examination object if the cutting plane of the axial sectional images is arranged orthogonally to the axis of symmetry of the water cylinder. The water-equivalent diameter can also be direction-dependent, in particular because the cross-section of the examination object is not usually circular. One method of calculating the water-equivalent diameter on the basis of an axial sectional image is known for example from the publication American Association of Physicists in Medicine (2014): "Use of Water Equivalent Diameter for Calculating Patient Size and Size-Specific Dose Estimates (SSDE) in CT (Task Group 220). Furthermore, the water-equivalent diameter can also be calculated on the basis of a topogram, for example by threshold value segmenting along a straight line.

In order to determine the water-equivalent diameter, the limits of the examination object are firstly determined in at least one of the X-ray images in the further dimension or in the further dimensions, preferably at the respective position in the head-foot direction. Integration over the Hounsfield Units of the respective X-ray image then takes place between the limits. The respective water-equivalent diameter is finally determined using the result of integration.

In some cases the X-ray image or at least one of the X-ray images is spatially-resolved in two further dimensions in addition to the head-foot direction. In this case the water-equivalent diameter is determined in a single slice of a three-dimensional scan. The slice is in this case oriented orthogonally to the head-foot direction. In many cases however, the X-ray image or at least one of the X-ray images is spatially-resolved in just a single further dimension in addition to the head-foot direction. As a rule, this further dimension will extend from left to right, based on the examination object, (what is referred to as an AP image, with AP standing for "anterior posterior"). The further direction can however alternatively likewise extend from front to back, based on the examination object (what is referred to as an LAT image, with LAT standing for "lateral"). In both cases—in other words, irrespective of whether the individual further dimension extends from left to right or from front to back,—a two-dimensional X-ray image is a topogram.

As a rule, the examination object is arranged on an examination table during acquisition of the X-ray images. For improved determination of the water-equivalent diameter, the examination table is preferably removed from at least one of the X-ray images before determination of the water-equivalent diameters. With an AP image this can take place in that the Hounsfield Units of the corresponding X-ray image are corrected before determination of the water-equivalent diameter by the basically known absorption of the examination table. With an LAT image this can take place in that a demarcation is performed. The demarcation can occur manually in the individual case. It preferably occurs automatically.

In the case of a two-dimensional X-ray image, the further dimension, as already mentioned, as a rule extends from left to right based on the examination object. In this case the corresponding X-ray image can also include the arms of the examination object. The arms of the examination object are preferably also removed from this X-ray image before determination of the water-equivalent diameters.

In the case of at least one two-dimensional X-ray image, a three-dimensional scan of the examination object is often also carried out following acquisition of the two-dimensional X-ray image or the two-dimensional X-ray images via the X-ray equipment. In this case, the water-equivalent diameters of the examination object determined using the two-dimensional X-ray images can be used during the three-dimensional scan in conjunction with settings of the X-ray equipment when performing the three-dimensional scan to determine a dose value (SSDE=size specific dose estimate) based on the size of the examination object. In this case, using the dose values based on the size of the examination object, it can also be decided whether an alarm is output to a user of the X-ray equipment or not. This prevents the often superfluous alarms, which are triggered in the prior art on the basis of what is known as CTDIVOL.

When determining the water-equivalent diameters of the examination object, a position of an examination table within a plane oriented orthogonally to the head-foot direction is preferably also considered, in particular a height of the examination table. The values required for this can alternatively be specified by a user or determined automatically using the data associated with the X-ray image.

During the course of the evaluation method, after determination, the determined, water-equivalent diameters of the examination object are preferably checked for plausibility by comparison with each other and/or with predefined values or values determined in some other way. In particular, successive water-equivalent diameters of the examination object determined in the head-foot direction can be examined for jumps and the determined, water-equivalent diameters of the examination object can also be checked for plausibility as such or in conjunction with the position in the head-foot direction using predetermined values.

It is possible to perform the evaluation using locally stored data. Preferably, however, the X-ray images are retrieved from a cloud and/or the water-equivalent diameters of the examination object are stored in the cloud.

With cloud computing, a provider makes computing power available in packets. For example, a total of approximately 10,000 physical computers are available to a provider at a particular location on earth. Each physical computer has a number of computer cores (CPUs), for example 16 computer cores. The physical computers also each have a working memory and a hard disk storage unit or comparable storage units, for example 128 GB working memory and 3 TB hard disk storage unit. The computer cores of the respective computer dynamically share the respective working memory and the respective hard disk storage unit. The physical computers can be arranged for example in 40-foot standard containers. In at least one further container of this kind there is arranged a central data storage unit, which comprises for example several 10 TB database clusters, which are each formed from a system of a plurality of hard disks and specialized database computers. This container is also arranged at said location. The containers can be permanently closed. They only require connections for the power supply, cooling and communication amongst themselves and with the Internet or World Wide Web.

The provider provides groups of computers, which are conventionally called virtual machines. Requirements for virtual machines are received from a cloud computer that manages the virtual machines. The requirements are provided by computers of computer networks and transmitted over the Internet to the cloud computer. The cloud computer then reserves the respectively demanded quantity of virtual machines for the respective requirement and transmits the corresponding access data to the computer making the demand in each case, so the corresponding virtual machines can be accessed from the respective computer network. The reservation for the respective requirement is retained until an approval is transmitted to the cloud computer by the computer of the computer network making the demand.

The evaluation method is preferably carried out completely automatically.

At least one embodiment is also directed to a computer program and/or non-transitory computer readable medium. According to at least one embodiment of the invention, processing of the machine code by the arithmetic device, causes the arithmetic device to carry out at least one embodiment of an inventive evaluation method.

At least one embodiment is also directed to an arithmetic device. According to at least one embodiment of the invention, the arithmetic device is programed with an least one embodiment of an inventive computer program, so during operation it carries out at least one embodiment of an inventive evaluation method.

Figure 1:
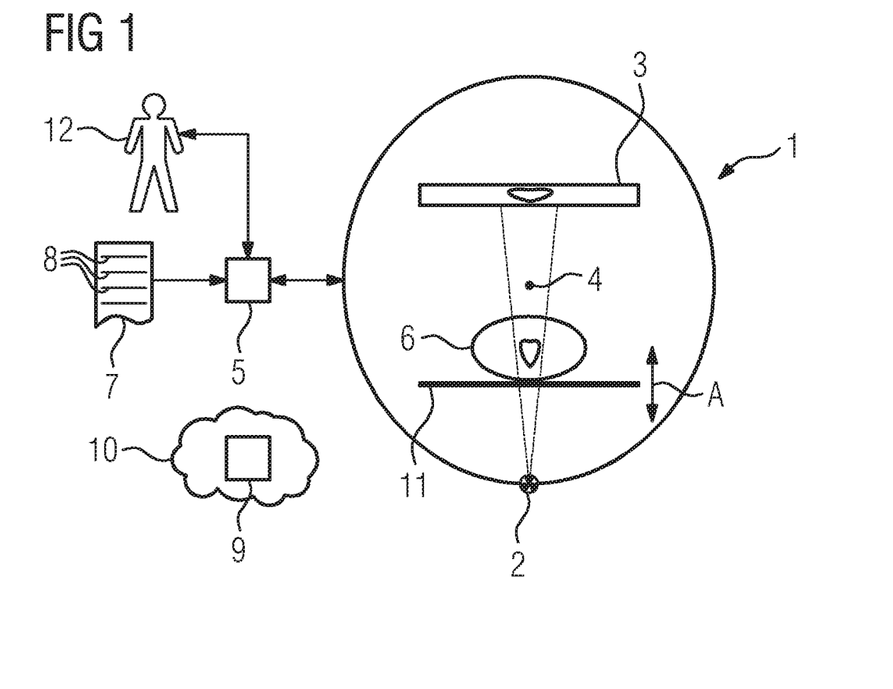
FIG. 1 shows X-ray equipment together with associated components.

According to FIG. 1 X-ray equipment 1 has an X-ray source 2 and an X-ray detector 3. The X-ray source 2 and X-ray detector 3 can often be rotated together about an axis of rotation 4. The X-ray detector 3 is often planar in design, in other words, acquires a two-dimensional image. X-ray images B of a human examination object 6 acquired via an arithmetic device 5 shall be evaluated via the X-ray equipment 1.

The arithmetic device 5 is programed with a computer program 7. The computer program 7 comprises machine code 8, which can be processed by the arithmetic device 5. Processing of the machine code 8 by the arithmetic device 5 causes the arithmetic device 5 to carry out an evaluation method illustrated in more detail below.

Figure 2:
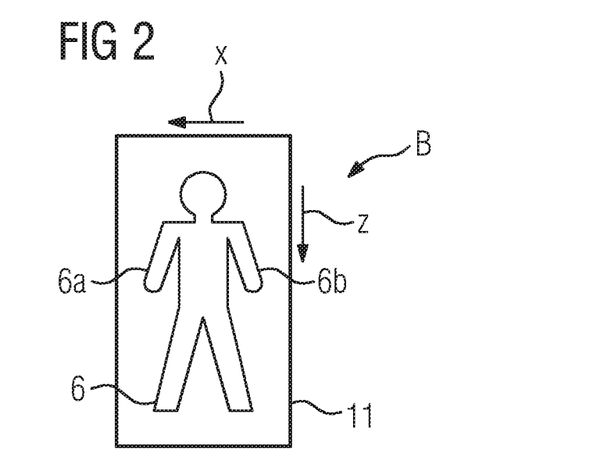
FIG. 2 shows an AP image.
Figure 3:
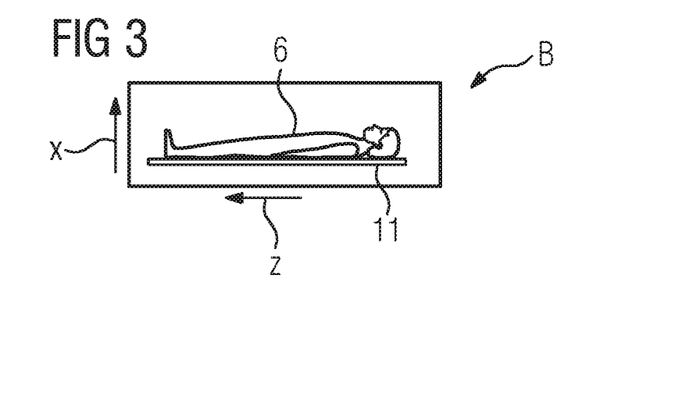
FIG. 3 shows an LAT image.
Figure 4:
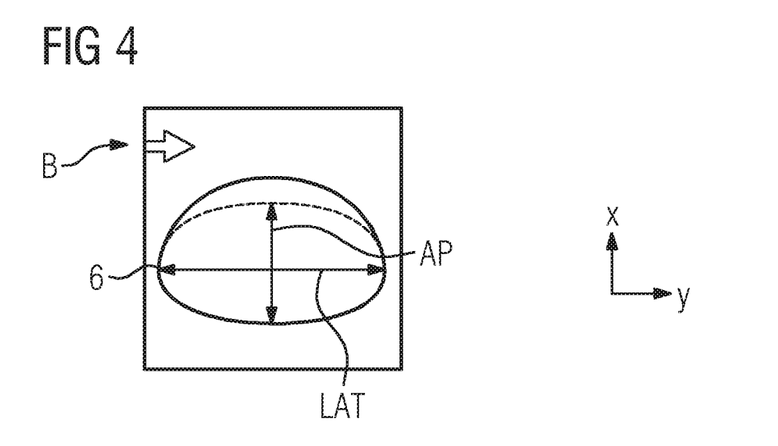
FIG. 4 shows a sectional image.

FIGS. 2 to 4 shows various X-ray images B. In all cases the X-ray image B of FIGS. 2 to 4 is spatially-resolved in a plurality of dimensions. One dimension—hereinafter called the z direction—extends in the head-foot direction of the examination object 6. If the X-ray image B is spatially-resolved in a single further dimension in addition to the z direction, the X-ray image B is a topogram. In this case the further direction—hereinafter called the x direction—can alternatively extend from left to right or from front to back. X-ray images B of this kind are generally known to persons skilled in the art and are conventionally called an AP image or an LAT image respectively. In both cases the further dimension is orthogonal to the z direction. FIG. 2 shows purely by way of example an AP image, FIG. 3 an LAT image. If the X-ray image B is spatially-resolved in two further dimensions in addition to the z direction, it is a sectional image of a three-dimensional computer tomogram. The sectional image as such is only two-dimensional. It is removed from the larger, three-dimensional computer tomogram, however. FIG. 4 shows purely by way of example an X-ray image B of this kind. The two further dimensions are in this case both orthogonal to the z direction and also orthogonal to each other. They are designated by x and y in FIG. 4.

Figure 5:
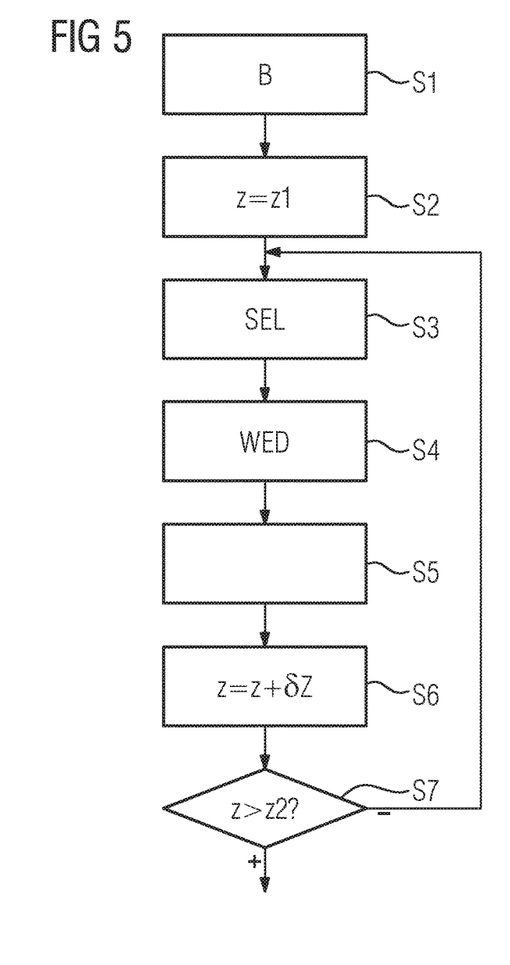
FIG. 5 shows a flowchart.

For evaluation, according to the illustration in FIG. 5, the X-ray images B are firstly acquired in a step S1 or—if the X-ray images B have already been acquired—the X-ray images B are retrieved from a storage unit 9 (see FIG. 1). The storage unit 9 is preferably a component of a cloud 10. In this case, the X-ray image B is therefore retrieved from the cloud 10.

In a step S2 the arithmetic device 5 sets the position in the z direction to a start value z1. The start value z1 is preferably chosen in such a way that it lies above the head of the examination object 6.

In a step S3 the arithmetic device 5 selects that part of at least one of the X-ray images B, which is located in the z direction at the corresponding position. In a step S4 the arithmetic device 5 determines for the instantaneous position in the z direction the relevant body region of the examination object 6, for example the contour of the head, the chest, the abdominal area or the pelvic region. Based on this, the arithmetic device 5 then determines for the relevant body region of the examination object 6 a water-equivalent diameter WED of the examination object 6. The determination is made in a plane orthogonal to the z direction. In particular, according to the illustration in FIG. 6, the arithmetic device 5 can determine the limits x1, x2 of the examination object 6 in the X-ray image B at the respective position in the z direction firstly in the further dimension or in the further dimensions and then integration over the Hounsfield Units HU of the X-ray image B can take place between the limits x1, x2. The result of integration can then be easily converted into the water-equivalent diameter WED of the examination object 6 at this position in the z direction.

Figure 6:
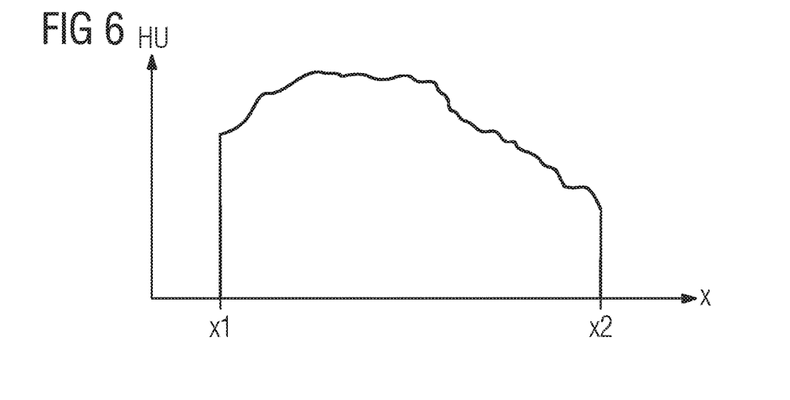
FIG. 6 shows a line of an X-ray image.

FIG. 6 shows the case where the evaluated X-ray image B is two-dimensional, in other words, extends in only a single further dimension in addition to the z direction (designated by x in FIG. 6). In this case the limits x1, x2 of the examination object 6 are a function of the position in the z direction. The procedure can, however, also be readily expanded to the case where the evaluated X-ray image B is three-dimensional, in other words, extends in two further dimensions in addition to the z direction (hereinafter designated by x and y). In this case the limits x1, x2 of the examination object 6 in the x direction are a function of the position in the z direction; the limits y1, y2 in the y direction are a function of the position in the z direction as well as the position in the x direction.

The arithmetic device 5 stores the determined, water-equivalent diameter WED in a step S5 by allocation to the X-ray images B and the respective position in the z direction. Analogously to retrieval of the X-ray images B in step S1, local storage is also possible here. Storage is preferably in the cloud 10, however.

In a step S6 the arithmetic device 5 increases the position in the z direction by an increment δz. The increment is constant in the context of the procedure of FIG. 5. As a rule, it is in the range of 1 to 2 mm, in some cases even below 1 mm. In a step S7 the arithmetic device 5 checks whether the position in the z direction has achieved or exceeded an end value z2. As a rule, the end value z2 is chosen in such a way that it is below the feet of the examination object 6.

If the end value z2 has still not been exceeded, the arithmetic device 5 returns to step S3. Otherwise the procedure of FIG. 5 is complete.

As can be seen from FIGS. 2 and 3, (and is also valid for FIG. 4), the examination object 6 is arranged on an examination table 11 during acquisition of the X-ray images B. The procedure of FIG. 5 is therefore preferably modified according to the illustration in FIG. 7.

Figure 7:
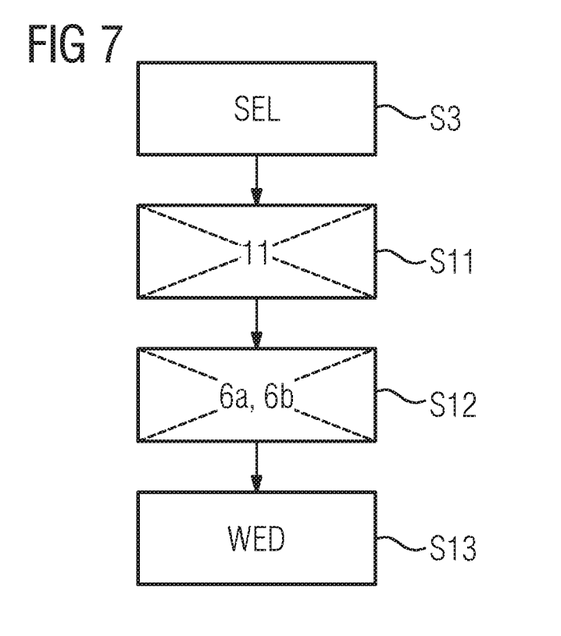
FIG. 7 shows a flowchart.

According to FIG. 7, a step S11 precedes step S4. In step S11 the examination table 11 is removed from the evaluated X-ray image B. In the case of an AP image (FIG. 2), this can occur in that the pixel values of the corresponding line of the evaluated X-ray image B are corrected by the attenuation, which is caused by the examination table 11. Appropriate correction values can for example be determined in advance. In the case of an LAT image (FIG. 3), this can occur in that the limits x1 or x2 between the examination object 6 and the examination table are determined accordingly. The corresponding limit x1 or x2 can be determined automatically. The examination table 11 can also be removed analogously in the case of a sectional image (FIG. 4).

With an AP image (FIG. 2, standard case) there can also be a step S12, corresponding to the illustration in FIG. 7, in which the arms 6a, 6b of the examination object are also removed from the X-ray image B.

Steps S11 and S12 can be implemented alternately. They can also be implemented together, however.

The examination table 11 and, connected herewith, also the examination object 6, viewed orthogonally to the z direction, are not always located at the same position. In particular, it is often possible to adjust the height of the examination table 11, indicated in FIG. 1 by a double arrow A. In some cases a lateral displacement of the examination table 11 can also be possible. The height positioning of the examination table 11, and to a lesser extent also the lateral positioning of the examination table 11, have an effect on the determination of the water-equivalent diameter WED. Alternatively or additionally to steps S11 and S12, it is therefore possible according to the illustration in FIG. 7, to replace step S4 with a step S13. Step S13 corresponds in terms of approach to step S4. In addition, the position of the examination table 11 within a plane oriented orthogonally to the z direction is considered. The corresponding specifications can be made to the arithmetic device 5 if required by a user 12 (see FIG. 1) or be information, which is allocated to the X-ray images B and can be automatically evaluated by the arithmetic device 5.

Figure 8:
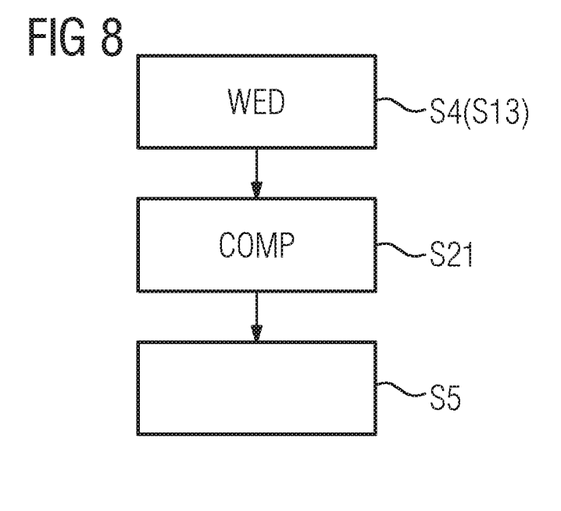
FIG. 8 shows a flowchart and
FIG. 9 shows a flowchart.

It is possible to store the determined, water-equivalent diameters WED, as they have been determined, in the storage unit 9. A step S21 preferably precedes step S5 according to the illustration in FIG. 8, however. In step S21 the arithmetic device 5 checks the determined, water-equivalent diameters WED of the examination object 6 for plausibility by comparison with each other and/or with predefined values or values determined in some other way.

In many cases, following acquisition of at least one two-dimensional X-ray image B (in other words, a topogram) via the X-ray equipment 1, a three-dimensional scan of the examination object 6 is carried out. The examination object 6 remains on the examination table 11 here in the period between acquisition of the at least one X-ray image B and performance of the three-dimensional scan. In this case it is possible to expand and supplement the procedure of FIG. 5 according to the illustration in FIG. 9.

Figure 9:
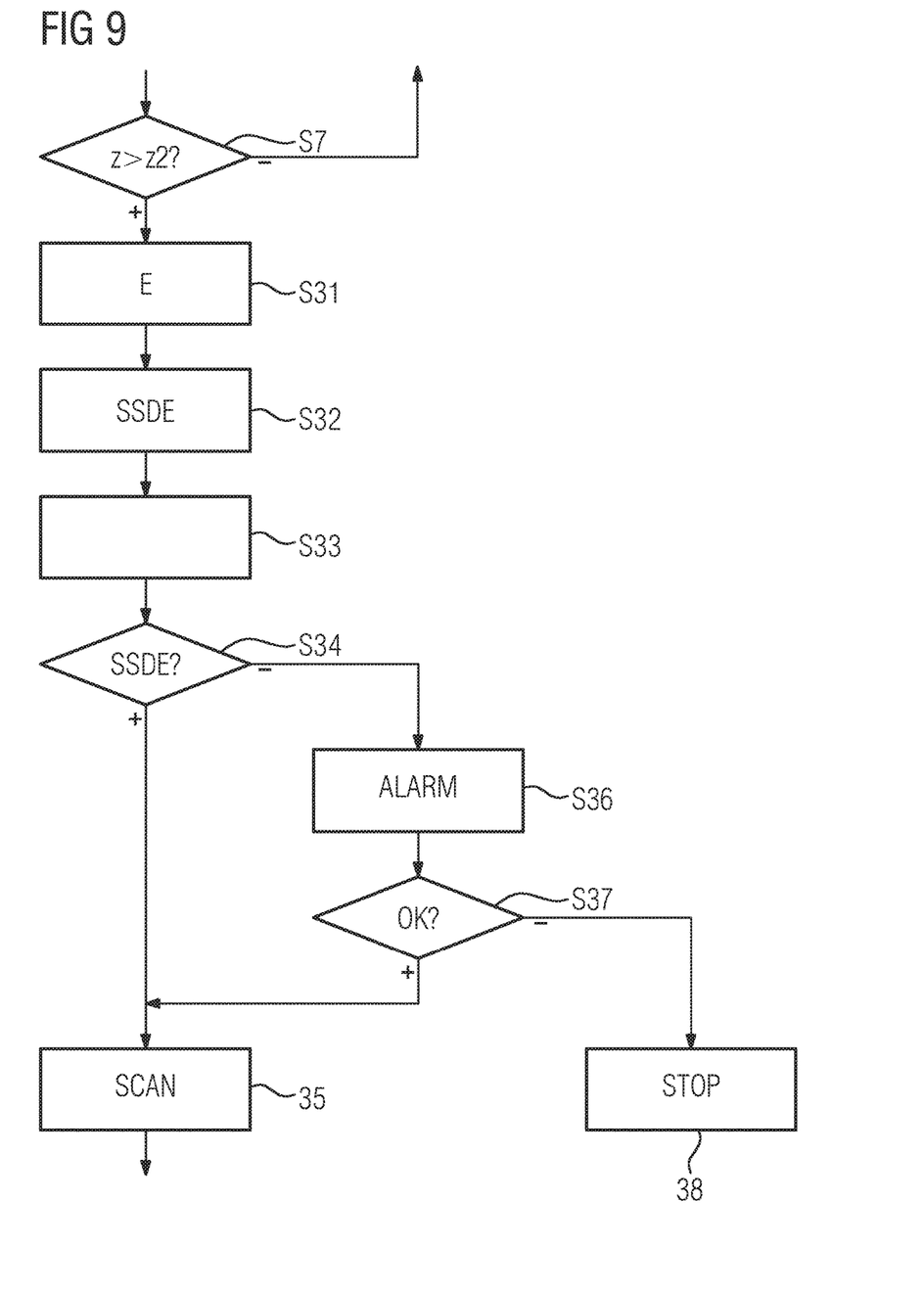

According to FIG. 9, steps S31 to S33 follow step S7. In step S31 settings E of the X-ray equipment 1, with which the X-ray equipment 1 is to be operated during performance of the three-dimensional scan, are known to the arithmetic device 5. For example, the settings E of the arithmetic device 5 can be specified by the user 12. In step S32 the arithmetic device 5 determines a dose value SSDE using the previously determined, water-equivalent diameters WED of the examination object 6 in conjunction with the settings E of the X-ray equipment. The dose value SSDE is based on the size of the examination object 6. It indicates to what extent the examination object 6 will be exposed to X-ray radiation during the three-dimensional scan. The arithmetic device 5 outputs the determined dose value SSDE to the user 12 in step S33.

In addition, according to the illustration in FIG. 9, steps S34 to S38 can exist. In step S34 the arithmetic device 5 checks whether an alarm should be output to the user 12. The checking of step S34 occurs by way of comparison of the determined dose value SSDE with a predetermined limit value. If no alarm is to be output, the arithmetic device 5 skips to step S35. The three-dimensional scan is performed in step S35. Otherwise the arithmetic device 5 skips to step S36. The alarm is output in step S36.

In step S37 the arithmetic device 5 checks whether an acknowledgement has been specified to it by the user 12. If this is the case, the arithmetic device 5 skips to step S35. Otherwise the arithmetic device 5 skips to step S38. In step S38 the three-dimensional scan is aborted before its implementation.

To summarize, the present invention therefore relates to the following facts:

X-ray images B of a human examination object 6 acquired via X-ray equipment 1 are each spatially-resolved in a plurality of dimensions. In each case one dimension extends in the head-foot direction of the examination object 6. The respective body region is detected in the X-ray images B in steps that are equidistant [in] the head-foot direction and, based on this, the water-equivalent diameter WED of the examination object 6 is determined in a plane orthogonal to the head-foot direction in each case. The water equivalent diameters WED determined for the respective position z are stored with allocation to the X-ray images B and the respective position z in the head-foot direction.

Embodiments of the present invention have many advantages. In particular, it is possible to determine the water-equivalent diameter of the examination object 6 easily and in a manner covering all manufacturers. Potential error sources (arms 6a, 6b, examination table 11, etc.) can be automatically considered. Conversion into meaningful SSDE values and an alarm check based heron are possible. The values can in particular be stored in the cloud 10 and are consequently available long-term and in principle internationally for statistical or individual evaluations. The water-equivalent diameter WED of the examination object 6 can be determined for any type of X-ray images B (AP images as well as LAT images and sectional images), and, more precisely, in the z direction with high spatial resolution.

Embodiments of the inventive evaluation method can be carried out at any time if the underlying X-ray image B has already been acquired. In particular, the evaluation in the case of a topogram can therefore be made both before and after performance of a subsequent three-dimensional scan. With a three-dimensional scan the evaluation can of course be made only after performance of the scan. The underlying X-ray images can exist locally as required, be retrieved from a PACS or be stored in the cloud 10. Furthermore, a plurality of X-ray images B can also be evaluated together. For example, with at least two two-dimensional X-ray images B, of which at least one is an AP image and one an LAT image, viewed in the z direction, the AP image can be evaluated in a first region and the LAT image can be evaluated in a second region. The second region can in particular be complementary to the first region here. Other combined evaluations of a plurality of X-ray images B are also possible.

Further example embodiments of the invention will be described below:

A first example embodiment of the invention is an evaluation method for a number of X-ray images (B) of a human examination object (6) acquired via X-ray equipment (1), wherein the X-ray images (B) are each spatially-resolved in a plurality of dimensions, wherein in each case one dimension extends in the head-foot direction of the examination object (6), wherein in each case the respective body region is detected in the X-ray images (B) in steps that are equidistant [in] the head-foot direction and, based on this, the water-equivalent diameter (WED) of the examination object (6) is determined in a plane orthogonal to the head-foot direction and wherein the water-equivalent diameters (WED) determined for the respective position (z) are stored with allocation to the X-ray images (B) and the respective position (z) in the head-foot direction.

A second example embodiment of the invention is an evaluation method according to the the first example embodiment, wherein at the respective position (z) in the head-foot direction firstly the limits (x1, x2, y1, y2) of the examination object (6) are determined in at least one X-ray image (B) in the further dimension or in the further dimensions, in that integration over the Hounsfield Units (HU) of the respective X-ray image (B) takes place between the limits (x1, x2, y1, y2) and in that the respective water-equivalent diameter (WED) is determined using the result of integration.

A third example embodiment of the invention is an evaluation method according to the first or the second example embodiment, wherein t the X-ray image (B) or at least one of the X-ray images (B) is spatially-resolved in two further dimensions in addition to the head-foot direction.

A fourth example embodiment of the invention is an evaluation method according to the first or the second example embodiment, wherein the X-ray image (B) or at least one of the X-ray images (B) is spatially-resolved in a single further dimension in addition to head-foot direction.

A fifth example embodiment of the invention is an evaluation method according to the fourth example embodiment, wherein during acquisition of the X-ray images (B), the examination object (6) is arranged on an examination table (11) and in that the examination table (11) is removed from at least one of the X-ray images (B) before determination of the water-equivalent diameters (WED).

A sixth example embodiment of the invention is an evaluation method according to the fourth or fifth example embodiment, wherein the further dimension, based on the examination object (6), extends from left to right and in that the arms (6a, 6b) of the examination object (6) are removed from this X-ray image (B) before determination of the water-equivalent diameters (WED).

A seventh example embodiment of the invention is an evaluation method according to the fourth, fifth or sixth example embodiment, wherein, following acquisition of the two-dimensional X-ray image (B) or the two-dimensional X-ray images (B) via the X-ray equipment (1), a three-dimensional scan of the examination object (6) is carried out and in that the water-equivalent diameters (WED) of the examination object (6), determined using the two-dimensional X-ray images (B), are used during the three-dimensional scan in conjunction with settings (E) of the X-ray equipment (1) when performing the three-dimensional scan in order to determine a dose value (SSDE) based on the size of the examination object (6).

An eighth example embodiment of the invention is an evaluation method according to the seventh example embodiment, wherein, using the dose values (SSDE) based on the size of the examination object (6), a decision is made as to whether an alarm is output to a user (12) of the X-ray equipment (1) or not.

A ninth example embodiment of the invention is an evaluation method according to one of the example embodiments from the first example embodiment through to the eighth example embodiment, wherein when determining the water-equivalent diameters (WED) of the examination object (6), a position of an examination table (11) within a plane oriented orthogonally to the head-foot direction is considered.

A tenth example embodiment of the invention is an evaluation method according to one of the example embodiments of the first example embodiment through to the ninth example embodiment, wherein the determined, water-equivalent diameters (WED) of the examination object (6)

are checked for plausibility by comparison with each other and/or with specified values or values determined in some other way.

An eleventh example embodiment of the invention is an evaluation method according to one of the example embodiments from the first example embodiment through to the tenth example embodiment, wherein the X-ray images (B) are retrieved from a cloud (10) and/or in that the water-equivalent diameters (WED) of the examination object (6) are stored in the cloud (10).

A twelfth example embodiment of the invention is an evaluation method according to one of the example embodiments from the first example embodiment through to the eleventh example embodiment, wherein it is carried out completely automatically.

A thirteenth example embodiment of the invention is a computer program for an arithmetic device (5), wherein the computer program comprises machine code (8), which can be processed by the arithmetic device (5), wherein processing of the machine code (8) by the arithmetic device (5) causes the arithmetic device (5) to carry out an evaluation method as discussed in one of the above embodiments.

A fourteenth example embodiment of the invention is an arithmetic device, which is programed with a computer program (7) according to the thirteenth example embodiment, so during operation it carries out an evaluation method according to one of the example embodiments from the first example embodiment through to the twelfth example embodiment.

Although the invention has been illustrated and described in detail by the preferred example embodiment, it is not restricted by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An evaluation method for a number of X-ray images of a human examination object acquired via X-ray equipment, the evaluation method comprising:
    spatially resolving each of the X-ray images in exactly two dimensions, including images of arms of the human examination object, wherein, based on the human examination object, one dimension of the two dimensions extends in a head-foot direction and a further dimension of the two dimensions extends from left to right;
    detecting, in each case, a respective body region in the X-ray images in steps equidistant in the head-foot direction;
    determining, based on the detecting, water-equivalent diameters of the human examination object in a plane orthogonal to the head-foot direction; and
    storing the water-equivalent diameters determined for each respective position with allocation to the X-ray images and to each respective position in the head-foot direction, wherein the images of the arms of the human examination object are removed from the X-ray images before the determining of the water-equivalent diameters, wherein, following the spatially resolving of the X-ray images via the X-ray equipment, a three-dimensional scan of the human examination object is carried out, wherein the water-equivalent diameters of the human examination object, determined using two-dimensional X-ray images of the X-ray images spatially resolved in exactly two dimensions, are used during the three-dimensional scan in conjunction with settings of the X-ray equipment when performing the three-dimensional scan in order to determine a dose value based on a size of the human examination object, and wherein, during the determining of the water-equivalent diameters of the human examination object, a position of an examination table within a plane oriented orthogonally to the head-foot direction is considered.

2. The evaluation method of claim 1, wherein, in a case of the respective position in the head-foot direction, firstly limits of the examination object are determined in at least one X-ray image in the further dimension or in other further dimensions, wherein integration over the Hounsfield Units of the respective X-ray image takes place between the limits and wherein the respective water-equivalent diameter is determined using the result of integration.

3. The evaluation method of claim 2, wherein, during acquisition of the X-ray images, the human examination object is arranged on an examination table, the examination table being later removed from at least one of the X-ray images before the determining of the water-equivalent diameters.

4. The evaluation method of claim 2, wherein each of the water-equivalent diameters of the human examination object respectively determined are checked for plausibility by comparison with at least one of other of the respectively determined water-equivalent diameters, specified values, or values determined in some other way.

5. The evaluation method of claim 2, wherein at least one of
    the X-ray images are retrieved from a cloud, and
    the water-equivalent diameters of the human examination object are stored in the cloud.

6. The evaluation method of claim 2, wherein the evaluation method is carried out completely automatically.

7. A non-transitory computer readable medium including machine code, processable by an arithmetic device, wherein processing of the machine code by the arithmetic device is configured to cause the arithmetic device to carry out the evaluation method of claim 2.

8. The evaluation method of claim 1, wherein, during the spatially resolving of the X-ray images, the human examination object is arranged on an examination table, the examination table being later removed from at least one of the X-ray images before the determining of the water-equivalent diameters.

9. The evaluation method of claim 1, wherein during determination of dose values based on the size of the human examination object, a decision is made as to whether or not to output an alarm to a user of the X-ray equipment.

10. The evaluation method of claim 1, wherein each of the respectively determined water-equivalent diameters of the human examination object are checked for plausibility by comparison with at least one of other of the respectively determined water-equivalent diameters, specified values, or values determined in some other way.

11. The evaluation method of claim 1, wherein at least one of
   the X-ray images are retrieved from a cloud, and
   the water-equivalent diameters of the human examination object are stored in the cloud.

12. The evaluation method of claim 1, wherein the evaluation method is carried out completely automatically.

13. A non-transitory computer readable medium including machine code, processable by an arithmetic device, wherein processing of the machine code by the arithmetic device is configured to cause the arithmetic device to carry out the evaluation method of claim 1.

14. An arithmetic device, comprising:
   at least one processor configured to
      spatially resolve X-ray images in exactly two dimensions, including images of arms of a human examination object, wherein, based on the human examination object, one dimension of the two dimensions extends in a head-foot direction and a further dimension of the two dimensions extends from left to right;
      detect, in each case, a respective body region in the X-ray images in steps equidistant in the head-foot direction;
      determine, based on the respective body region detected, water-equivalent diameters of the human examination object in a plane orthogonal to the head-foot direction; and
      store the water-equivalent diameters determined for each respective position with allocation to the X-ray images and to each respective position in the head-foot direction, wherein the images of the arms of the human examination object are removed from the X-ray images before determining the water-equivalent diameters, wherein, following the spatially resolving of the X-ray images, a three-dimensional scan of the human examination object is carried out; wherein the water-equivalent diameters of the human examination object, determined using two-dimensional X-ray images of the X-ray images spatially resolved in exactly two dimensions, are used during the three-dimensional scan in conjunction with settings of X-ray equipment when performing the three-dimensional scan in order to determine a dose value based on a size of the human examination object; and wherein, during the determining of the water-equivalent diameters of the human examination object, a position of an examination table within a plane oriented orthogonally to the head-foot direction is considered.

* * * * *